United States Patent
Green

(10) Patent No.: US 9,857,335 B2
(45) Date of Patent: Jan. 2, 2018

(54) ION MOBILITY SPECTROMETER

(71) Applicant: Micromass UK Limited, Wilmslow (GB)

(72) Inventor: Martin Raymond Green, Bowdon (GB)

(73) Assignee: MICROMASS UK LIMITED, Stamford (GB)

( * ) Notice: Subject to any disclaimer, the term of this patent is extended or adjusted under 35 U.S.C. 154(b) by 0 days.

(21) Appl. No.: 15/160,050

(22) Filed: May 20, 2016

(65) Prior Publication Data

US 2016/0341696 A1 Nov. 24, 2016

(30) Foreign Application Priority Data

May 22, 2015 (GB) .................................. 1508821.4

(51) Int. Cl.
| | | |
|---|---|---|
| *G01N 27/62* | (2006.01) | |
| *H01J 49/04* | (2006.01) | |
| *H01J 49/24* | (2006.01) | |
| *H01J 49/00* | (2006.01) | |

(52) U.S. Cl.
CPC .......... *G01N 27/622* (2013.01); *H01J 49/004* (2013.01); *H01J 49/0468* (2013.01)

(58) Field of Classification Search
CPC .......................... G01N 27/622; H01J 49/0031; H01J 49/0404; H01J 49/24; H01J 49/26; H01J 49/28; H01J 49/34
USPC .................................. 250/281, 282, 283, 290
See application file for complete search history.

(56) References Cited

U.S. PATENT DOCUMENTS

| | | |
|---|---|---|
| 7,388,197 B2 | 6/2008 | McLean et al. |
| 7,629,177 B2 | 12/2009 | Davis et al. |
| 8,507,852 B2 | 8/2013 | Makarov |
| 2016/0305907 A1* | 10/2016 | Green .................. G01N 27/622 |

* cited by examiner

*Primary Examiner* — Nicole Ippolito

(57) ABSTRACT

There is provided a method of separating ions comprising operating an ion mobility spectrometer or separator at a reduced pressure and at an operating temperature less than 40° C., and providing a drift gas within said ion mobility spectrometer or separator, wherein said drift gas comprises one or more substances that exist as a liquid at atmospheric pressure (optionally about 1013 mbar) and room temperature (optionally about 20° C.) and wherein said one or more substances have a boiling or sublimation point less than said operating temperature of said ion mobility spectrometer or separator, at said reduced pressure.

30 Claims, 6 Drawing Sheets

ION MOBILITY SPECTROMETER

CROSS-REFERENCE TO RELATED APPLICATION

This application claims priority from and the benefit of United Kingdom patent application No. 1508821.4 filed on 22 May 2015. The entire content of this application is incorporated herein by reference.

FIELD OF THE INVENTION

The present invention relates generally to ion mobility spectrometry and in particular to ion mobility spectrometers or separators and methods of ion mobility spectrometry.

BACKGROUND

Introduction of volatile liquid additives to an ion mobility buffer gas is known in ion mobility spectrometry ("IMS") devices that operate at atmospheric pressure. Liquid additives can be introduced as a vapour into the buffer gas stream, and the drift gas of the ion mobility separation device may comprise buffer gas as well as the additives dispersed therein. The volatility range and mol fraction of the additive as a proportion of the drift gas composition may be limited to avoid condensation of the additive within the ion mobility separation device. The ion mobility separation device may need to be heated above the boiling point of the liquid additive in order to avoid condensation.

If condensation of the liquid additive occurs within the ion mobility separation device, the mol fraction of the additive in the drift gas cannot be accurately calculated and may not be constant throughout all separations. Consequently it can be difficult to quantitatively introduce liquid additives into atmospheric pressure ion mobility separation devices.

An improved method of separating ions in which one or more substances, for example liquid additives, are dispersed or otherwise present in the drift gas of an ion mobility separation device is desired.

SUMMARY

According to an aspect there is provided a method of separating ions comprising:

operating an ion mobility spectrometer or separator at a reduced pressure and at an operating temperature less than about 40° C.; and providing a drift gas within the ion mobility spectrometer or separator, wherein the drift gas comprises one or more substances that exist as a liquid at atmospheric pressure (optionally about 1013 mbar) and room temperature (optionally about 20° C.) and wherein the one or more substances have a boiling or sublimation point less than said operating temperature of said ion mobility spectrometer or separator, at said reduced pressure.

The one or more substances may remain in vapour form at the reduced pressure of the ion mobility spectrometer or separator. This means that condensation of the substances within the ion mobility spectrometer or separator will be eliminated or minimised. This allows a wider range of substances to be introduced into the ion mobility spectrometer or separator and/or in larger quantities.

The term "reduced pressure" as used herein may refer to sub-atmospheric or sub-ambient pressure, for example a pressure that is reduced compared to the environment outside of the ion mobility spectrometer or separator (or mass spectrometer containing the ion mobility spectrometer or separator).

The range referred to above (i.e. less than about 40° C.) may be seen as the range of typical room temperature values for an ion mobility spectrometer or separator that is not subject to heating. It has been recognised that the introduction of liquid additives into an ion mobility spectrometer or separator can be improved by operating the ion mobility spectrometer or separator at atmospheric temperature (or less than about 40° C.) and reducing the pressure. As stated above, this allows a wider range of substances or additives to be used without the need to heat the ion mobility spectrometer or separator.

The method may further comprise operating the ion mobility spectrometer or separator, or a drift region of the ion mobility spectrometer or separator, at a pressure less than about 10 mbar, 8 mbar, 6 mbar, 4 mbar or 2 mbar.

The one or more substances may be provided in varying degrees of concentration to achieve a certain ion mobility spectrometry ("IMS") selectivity. For example, a low percentage (e.g. less than about 1%) may be used, for example to introduce reagents as the one or more substances into the drift gas of the ion mobility spectrometer or separator. Alternatively, greater than about 90%, about 95% or substantially all of the gas within the ion mobility spectrometer or separator may consist of the one or more substances.

Between about 1-2%, about 2-4%, about 4-8%, about 8-16%, about 16-30%, about 30-40%, about 40-50%, about 50-60%, about 60-70%, about 70-80%, about 80-90% or about 90-100% of the drift gas may consist of the one or more substances.

The drift gas may further comprise a buffer gas. The one or more substances may comprise or consist of an additive or dopant to said buffer gas, which may be for IMS selectivity, for example of ions travelling through said ion mobility spectrometer or separator.

For example, the buffer gas may consist of or comprise nitrogen gas, and the one or more substances may comprise methanol. The one or more substances may comprise an additive that is introduced into the ion mobility spectrometer or separator, for example to increase the drift time of ions within the ion mobility spectrometer or separator.

The method may further comprise mixing the one or more substances with the buffer gas prior to introducing the buffer gas into the ion mobility spectrometer or separator, or keeping the one or more substances and the buffer gas separate prior to introducing the one or more substances and the buffer gas into the ion mobility spectrometer or separator.

The method may further comprise introducing the one or more substances into the ion mobility spectrometer or separator simultaneously or separately to the buffer gas.

The method may further comprise introducing the one or more substances into the ion mobility spectrometer or separator via a capillary. An entrance of the capillary may be at atmospheric temperature and/or pressure. The entrance of the capillary may extend into a liquid comprising the one or more substances in a liquid state.

The method may further comprise heating the capillary as the one or more substances are drawn through the capillary, to optionally assist vaporisation of the one or more substances prior to entering the ion mobility spectrometer or separator.

The capillary may be made from metal or a thermally-conductive material.

The step of heating the capillary may comprise resistively heating the capillary.

The method may further comprise drawing, for example continuously driving, pushing, propelling or drawing the one or more substances through the capillary using a pump, for example a pump external to the mass spectrometer or ion mobility spectrometer or separator, and/or using the pressure differential between a source of the one or more substances and the ion mobility spectrometer or separator.

The one or more substances may be caused to vapourise upon exiting the capillary due to the reduction in pressure between the capillary and the ion mobility spectrometer or separator, or due primarily to the reduction in pressure between the capillary and the ion mobility spectrometer or separator.

The method may further comprise applying energy to the capillary to assist vaporisation of the one or more substances within the capillary. The energy may comprise heat and/or ultrasound and/or electrostatic energy. The electrostatic energy may be applied using an electrode, for example a counter electrode positioned downstream of the capillary and/or adjacent an end of the capillary or delivery tube (described below).

The method may further comprise heating the capillary to assist vaporisation of the one or more substances, for example prior to the one or more substances entering the ion mobility spectrometer or separator. It should be noted that heating the capillary may not heat the ion mobility spectrometer or separator, within which the one or more substances may be held in gaseous form due to the reduced pressure therein.

The method may further comprise positioning the capillary within a delivery tube, wherein the delivery tube is in fluid communication with the ion mobility spectrometer or separator, and optionally exits or extends into the ion mobility spectrometer or separator. The capillary may be positioned coaxially within the delivery tube, or substantially coaxially within the delivery tube. The delivery tube may surround or partially surround the capillary, for example so as to be concentric with the capillary.

A chamber may be located downstream of the end of the capillary and/or delivery tube. The chamber may comprise an inlet in fluid communication with the capillary and/or delivery tube, and an outlet in fluid communication with the ion mobility spectrometer or separator. The outlet may be arranged and adapted to release drift gas directly into the ion mobility spectrometer or separator. The chamber may be located immediately after the delivery tube, or the chamber may form the downstream end of the delivery tube.

The chamber may have an increased diameter or cross-sectional area compared to the capillary and/or delivery tube. The outlet of the chamber may have a width (e.g., through a centre point of the outlet 24), diameter or cross-sectional area (for example a smallest width, diameter or cross-sectional area) that is less than that of the capillary and/or delivery tube. The outlet may have a width, diameter or cross-sectional area (for example a smallest width, diameter or cross-sectional area) that is less than 5%, 10%, 15% or 20% of the largest diameter or cross-sectional area of the chamber. The width, diameter or cross-sectional area (for example a smallest width, diameter or cross-sectional area) of the outlet may be less than 10%, 20%, 30%, 40%, 50%, 60%, 70%, 80% or 90% of the width, diameter or cross-sectional area (for example the smallest width, diameter or cross-sectional area) of the inlet.

In use a fluid may be travelling through the delivery tube, which fluid may be a drift gas and may include the one or more substances and/or a buffer gas. The fluid may enter the chamber through the inlet, and may expand, for example due to the increased volume (or width, diameter or cross-sectional area) of the chamber. The constituents of the fluid, for example the one or more substances and/or a buffer gas may intermix within the chamber. The fluid (e.g., once intermixed) may then pass through the outlet of the chamber and into (e.g., directly into) the ion mobility spectrometer or separator.

The method may further comprise introducing a or the buffer gas into the delivery tube. The buffer gas may be introduced into the delivery tube via a buffer gas inlet in the delivery tube. The buffer gas inlet may be positioned behind an exit of the capillary that is positioned within the delivery tube. The buffer gas may nebulise the liquid emerging from the capillary, for example by locating the outlet of the capillary substantially in the flow of the buffer gas.

The one or more substances may be held in a gaseous state within the ion mobility spectrometer or separator due to the reduced pressure of the ion mobility spectrometer or separator.

The ion mobility spectrometer or separator may not be heated, or may not be heated above atmospheric temperature, or may not be heated relative to its immediate exterior, or may not be heated by application of heat directly to the ion mobility spectrometer or separator, for example by a heater.

The one or more substances may be selected or provided such that they would transition to a liquid or solid state within the ion mobility spectrometer or separator if the ion mobility spectrometer or separator were operated at atmospheric pressure, and optionally kept or operated at the same temperature or less than about 40° C.

The ion mobility spectrometer or separator may comprise a plurality of electrodes, and the method may further comprise applying an AC or RF voltage to at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the electrodes forming the ion mobility spectrometer or separator in order to confine ions radially within the ion mobility spectrometer or separator.

The ion mobility spectrometer or separator may comprise a stacked ring ion guide comprising a plurality of electrodes, each having an aperture through which ions are transmitted in use. The spacing of the electrodes may increase along the length of the ion path, and the apertures in the electrodes in an upstream section of the ion guide may have a first diameter and the apertures in the electrodes in a downstream section of the ion guide may have a second diameter which is smaller than the first diameter. Opposite phases of an or the AC or RF voltage may be applied, in use, to successive electrodes.

In various embodiments, ions or excited metastables may be created during the vaporisation process and may interact with analyte ions during ion mobility separation. These may be produced, for example, by an electrospray process, glow discharge process, UV photo ionization process or electron bombardment process.

In accordance with an aspect there is provided a method of mass spectrometry or ion mobility spectrometry as described above or substantially as described herein, for example with reference to the figures.

In accordance with an aspect there is provided a device for separating ions comprising:

an ion mobility spectrometer or separator; and a control system arranged and adapted:

(i) to operate the ion mobility spectrometer or separator at a reduced pressure and at an operating temperature below 40° C.; and (ii) to provide a drift gas within the ion mobility spectrometer or separator, wherein the drift gas comprises one or more substances that exist as a liquid at atmospheric pressure (optionally about 1013 mbar) and room temperature (optionally about 20° C.) and wherein the one or more substances have a boiling or sublimation point less than said operating temperature of said ion mobility spectrometer or separator, at said reduced pressure.

In accordance with an aspect there is provided a mass spectrometer as described above or substantially as described herein, for example with reference to the figures.

The methods and apparatus described herein may be applicable to ion guides and traps as well as ion mobility spectrometers and separators. As such, in accordance with an aspect there is provided a method of guiding or trapping ions comprising:

operating an ion guide or ion trap at a reduced pressure and an operating temperature less than about 40° C.; and providing a gas within the ion guide or ion trap, wherein the gas comprises one or more substances that exist as a liquid at atmospheric pressure (optionally about 1013 mbar) and room temperature (optionally about 20° C.) and wherein the one or more substances have a boiling or sublimation point less than said operating temperature of said ion mobility spectrometer or separator, at said reduced pressure.

The one or more substances may comprise a sample to be ionised, or comprise ionised sample optionally to be analysed in a mass spectrometer.

The ion guide or ion trap may operate as an ion-molecule reaction device.

The method may further comprise reacting ions within said ion-molecule reaction device to form adduct or product ions. The step of reacting ions may comprise performing hydrogen-deuterium exchange within said ion-molecule reaction device.

In accordance with an aspect there is provided a device for guiding or trapping ions, comprising:

an ion guide or ion trap; and a control system arranged and adapted:

(i) to operate the ion guide or ion trap at a reduced pressure and an operating temperature below 40° C.; and (ii) to provide a gas within the ion guide or ion trap, wherein the gas comprises one or more substances that exist as a liquid at atmospheric pressure (optionally about 1013 mbar) and room temperature (optionally about 20° C.) and wherein the one or more substances have a boiling or sublimation point less than said operating temperature of said ion mobility spectrometer or separator, at said reduced pressure.

Sub-atmospheric ion mobility separation devices are known, wherein ions may be radially confined using RF confining potentials (pseudo-potentials) allowing high transmission, and high duty cycle when coupled to up-stream ion trapping. These devices may operate at between about 0.5 and about 10 mbar pressure. At these pressures many organic compounds which are liquids at room temperature exist as a gas or vapour at reduced pressure. It has been found that this may allow direct continuous infusion of liquids into an ion mobility separation device without the requirement for heating the device. It also allows the composition of the drift gas within the ion mobility separation device to be comprised of very high proportions, for example up to 100% of the liquid introduced, without condensation issues.

In accordance with an aspect there is provided a method of ion mobility separation comprising:

providing an ion mobility spectrometer or ion mobility separation ("IMS") device operating at a pressure below 10 mbar and a temperature below 40° C., wherein ions are optionally confined radially within the device during separation by means of a RF pseudo potential, and liquid sample is continuously introduced into the ion mobility separation device, the components of the liquid sample having a boiling point substantially above 40° C. at a pressure of <10 mbar.

A gaseous and liquid sample may be introduced simultaneously. The liquid sample may comprise a mixture of compounds. A heated nebuliser may be used at low pressure, for example to introduce the liquid sample into the ion mobility separation device. An ultrasonic nebuliser may be used at low pressure, for example to nebulise the liquid sample as it is introduced into the ion mobility separation device. A high voltage counter electrode may be used at low pressure, for example to assist nebulisation on its own, or in conjunction with the heated or ultrasonic nebuliser described above.

According to various embodiments pure compounds or mixtures of compounds which exist as a gas or vapour at a pressure below 10 mbar and the operating temperature of the mass spectrometer, but which exist as liquids at atmospheric or room temperature and pressure, are optionally introduced into the drift region of the ion mobility separation device with or without introduction of additional buffer gas, and may be introduced continuously. This may extend the range of ion mobility gas compositions which may be used to perform selective ion mobility separations.

The methods and apparatus disclosed herein may provide or comprise a mass spectrometer comprising one or more of an ion source, an ion guide or trap, a mass filter, a first collision gas cell, a second collision gas cell and a Time of Flight mass analyser.

The ion source may be an atmospheric pressure ion source. The ion guide or trap may be maintained at a reduced pressure, for example less than about 2 mbar, and optionally between about $10^{-3}$ and about 2 mbar. The mass filter may comprise a quadrupole mass filter and/or may be maintained at a reduced pressure, for example less than about $10^{-2}$ mbar, and optionally less than about $10^{-4}$ mbar. The first and/or second collision gas cell may be maintained at a reduced pressure, for example less than about $10^{-2}$ mbar, and optionally less than about $5 \times 10^{-3}$ mbar. The collision gas within the first or second collision gas cell may comprise argon. The ion mobility spectrometer or separator may comprise a drift cell and/or a vacuum chamber and/or may be maintained at less than about 10, 5 or 2 mbar of a drift gas, for example comprising nitrogen. The Time of Flight mass analyser may comprise an orthogonal acceleration Time of Flight mass analyser and/or may be maintained at a reduced pressure, for example less than about $10^{-4}$ or less than about $10^{-6}$ mbar.

The ion mobility spectrometer or separator may comprise a travelling wave ion mobility spectrometer or separator, or a travelling wave ion guide.

Any one of the ion source, ion guide or trap, mass filter, first collision gas cell and second collision gas cell may comprise a plurality of electrodes, and the method may further comprise applying an AC or RF voltage to at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% of the electrodes forming the ion mobility spectrometer or separator in order to confine ions radially within the ion mobility spectrometer or separator.

Any one of the ion source, ion guide or trap, mass filter, first collision gas cell and second collision gas cell may comprise a stacked ring ion guide comprising a plurality of electrodes, each having an aperture through which ions are transmitted in use. The spacing of the electrodes may increase along the length of the ion path, and the apertures in the electrodes in an upstream section of the ion guide may have a first diameter and the apertures in the electrodes in a downstream section of the ion guide may have a second diameter which is smaller than the first diameter. Opposite phases of an or the AC or RF voltage may be applied, in use, to successive electrodes.

As used herein, atmospheric or room temperature and pressure may refer to the ambient conditions of the mass spectrometer or ion mobility spectrometer or separator, and could be termed ambient temperature and pressure. The one or more substances may exist as a liquid outside of the mass spectrometer or ion mobility spectrometer or separator, e.g. at ambient temperature and pressure, and exist as a gas or vapour within the ion mobility spectrometer or separator. Atmospheric or room temperature may be about 20° C., and atmospheric pressure may be about 1013 mbar.

As used herein, 1 mbar may be equal to 100 pascals.

A reduced pressure may refer to a sub-atmospheric or sub-ambient pressure, for example a pressure that is reduced compared to the environment outside of the ion mobility spectrometer or separator (or mass spectrometer containing the ion mobility spectrometer or separator). The pressure inside the ion mobility spectrometer or separator may be actively reduced, for example using a vacuum pump.

The phase change to gas may be due only to the reduction in pressure between the ambient environment and the ion mobility spectrometer or separator, or may be assisted by an intermediate device (such as a heated capillary). However, the ion mobility spectrometer or separator itself may not be heated, and may be maintained at around ambient temperature and pressure, for example less than about 40° C., about 30° C., or about 20° C. As such, the one or more substances will not transition back to a liquid within the ion mobility spectrometer or separator, since their boiling or sublimation point is above the operating temperature of the ion mobility spectrometer or separator, at the reduced pressure.

The spectrometer may comprise an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; (xxviii) a Laser Ablation Electrospray Ionisation ("LAESI") ion source; and (xxix) Surface Assisted Laser Desorption Ionisation ("SALDI").

The spectrometer may comprise one or more continuous or pulsed ion sources.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The spectrometer may comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) C60 vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which.

DETAILED DESCRIPTION

The present disclosure may relate generally to a method of separating ions according to their ion mobility. The method may comprise operating an ion mobility spectrometer or separator at a reduced pressure and at an operating temperature less than 40° C., providing a drift gas within said ion mobility spectrometer or separator, wherein said drift gas comprises one or more substances that exist as a liquid at atmospheric pressure (optionally about 1013 mbar) and room temperature (optionally about 20° C.) and wherein said one or more substances have a boiling or sublimation point less than said operating temperature of said ion mobility spectrometer or separator, at said reduced pressure.

By operating an ion mobility spectrometer or separator in this manner, the introduction of liquid additives into the ion mobility spectrometer or separator can be improved. This is due to the operation of the ion mobility spectrometer or separator at atmospheric temperature (or less than about 40° C.) and a reduced pressure.

As discussed above and herein, this allows substances or additives to be incorporated into the drift gas of the ion mobility spectrometer or separator that are in liquid phase at room temperature and pressure.

In contrast to conventional arrangements, instead of heating the ion mobility spectrometer or separator in order to prevent such substances from condensing inside the ion mobility spectrometer or separator, the pressure of the ion mobility spectrometer or separator is reduced. This means that the liquid substances can be incorporated in the drift gas without the need to heat the ion mobility spectrometer or separator.

The reduced pressure of the ion mobility spectrometer or separator may be less than 10 mbar, or even lower as described herein. The pressure may be reduced to a value that is lower than that necessary to prevent the one or more substances from condensing inside the ion mobility spectrometer or separator at its operating temperature (e.g., about 20° C.).

The one or more substances may correspond to the majority of the drift gas, such that greater than about 90%, about 95% or substantially all of the gas within the ion mobility spectrometer or separator may consist of the one or more substances. Alternatively, the one or more substances may be an reagent or dopant, for example a reagent or dopant that is a liquid at room temperature and pressure, wherein a low percentage (e.g. less than about 5%, 4%, 3%, 2% or 1%) of the drift gas may consist of the reagent or dopant. In various embodiments, however, the one or more substances may be provided in varying degrees of concentration to achieve a certain ion mobility spectrometry ("IMS") selectivity.

The drift gas may be made up of a buffer gas and the one or more substances, and the one or more substances comprise an additive or dopant to said buffer gas for ion mobility spectrometry ("IMS") selectivity.

An embodiment of the present disclosure will now be described.

Figure 1:
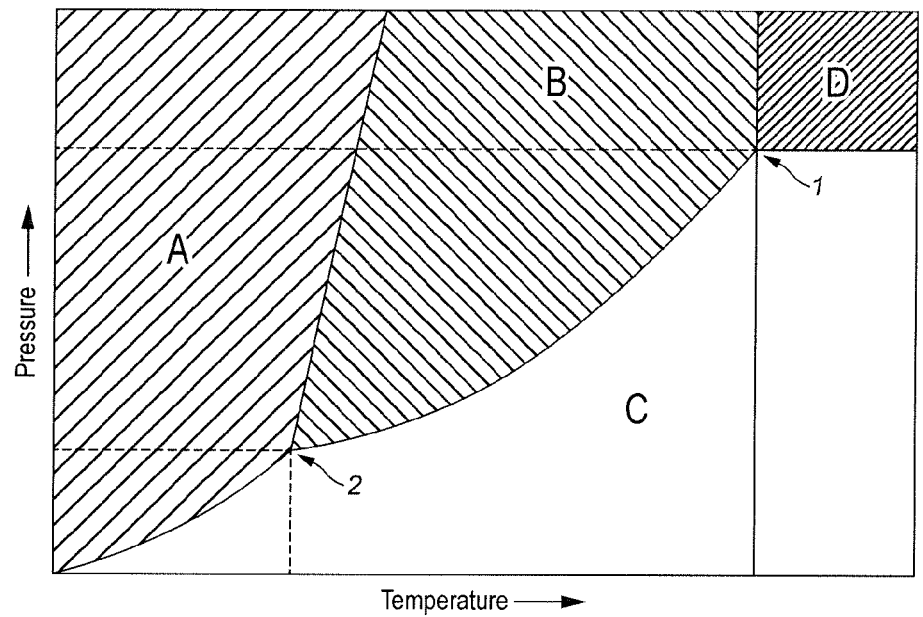
FIG. 1 shows a typical phase diagram of pressure versus temperature.

FIG. 1 shows a typical phase diagram of pressure verses temperature for a given compound. The shaded regions indicate the phase of the compound at different pressure and temperature values. Region A is solid phase, region B is liquid phase, region C is gas phase and region D is supercritical fluid phase.

The triple point 2 indicates the temperature and pressure at which the three phases (gas, liquid, and solid) of the compound coexist in thermodynamic equilibrium. The critical point 1 indicates where the boundary of liquid and gas phases cease to coexist.

Matter in the region C, below the critical point may be referred to as vapour. Vapour refers to a substance in the gas phase below the critical point, and which may be condensed into a liquid by raising the pressure. Regardless of this definition in common usage the terms vapour and gas are often used to mean the same thing.

Figure 2:
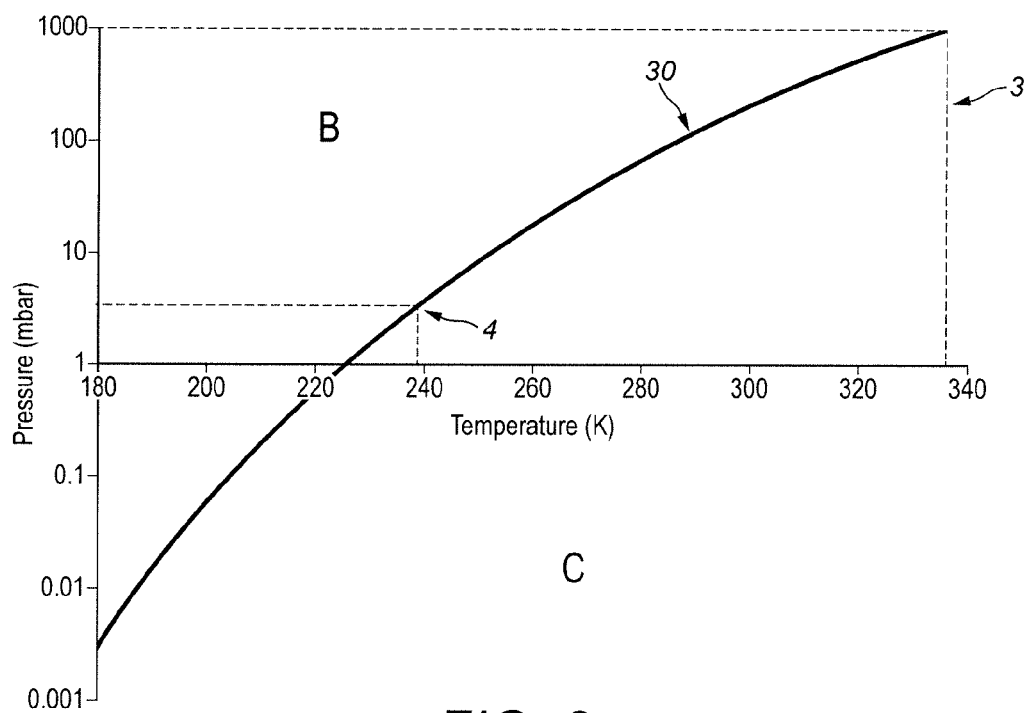
FIG. 2 shows a section of the phase diagram for methanol.

FIG. 2 shows part of a phase diagram for methanol. The y-axis indicates log pressure in mbar and the x-axis indicates temperature in Kelvin. In region B methanol exists as a liquid and in region C methanol exist as a gas or vapour. A line 30 indicates the boiling point of methanol for various values of temperature and pressure.

A first point 3 indicates the boiling point of methanol at atmospheric pressure (about 1000 mbar). The boiling point of methanol at about 1000 mbar may be about 337.7 K or about 64.7° C.

A second point 4 indicates the boiling point of methanol at about 5 mbar. This may be a typical operational pressure of an ion mobility spectrometer or separator operating at reduced pressure. At about 5 mbar the boiling point of methanol may be about 237 K or about −35° C.

From FIG. 2 it can be seen that methanol will typically exist as a vapour or gas at room temperature (about 25° C. or about 298 K), and below a pressure of about 175 mbar.

The boiling point of a liquid at reduced pressure may be calculated from the Clausius Clapeyron equation:

$$\ln\left(\frac{P1}{P2}\right) = \frac{-\Delta H}{R}\left(\frac{1}{T1} + \frac{1}{T2}\right) \quad (1)$$

wherein T1 is the boiling point at pressure P1, T2 is the boiling point at pressure P2, R is a gas constant and ΔH is the specific heat capacity in KJ/mol.

Figure 3:
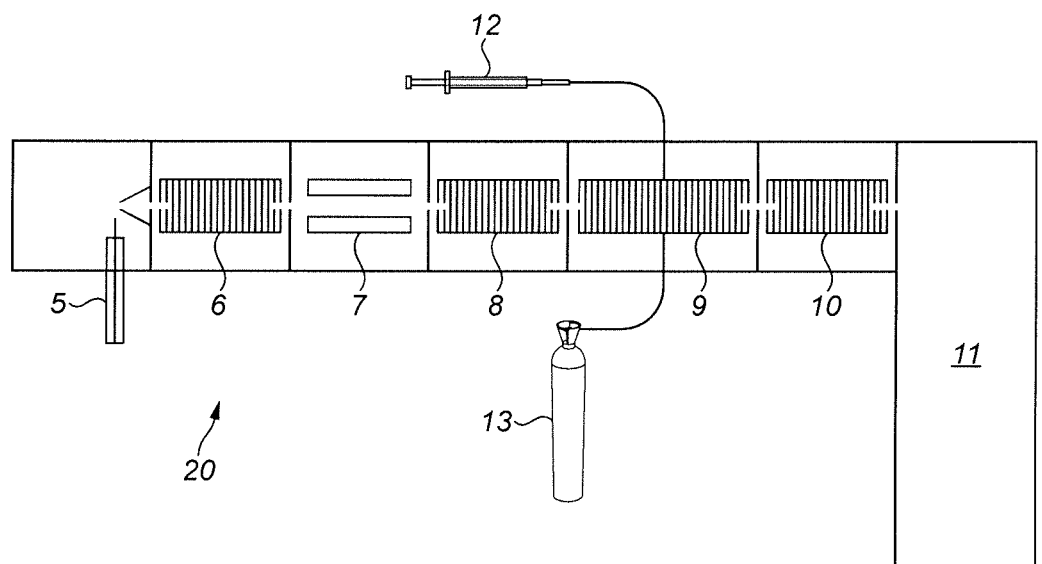
FIG. 3 shows a mass spectrometer according to an embodiment.

FIG. 3 shows a mass (and/or ion mobility) spectrometer 20 according to an embodiment of the present disclosure. This is one example of such an apparatus and the various features may be altered and/or modified whilst remaining within the broadest aspects of the present disclosure.

The mass spectrometer 20 may comprise one or more of an ion source 5, a mass filter 7, a first collision gas cell 8, an ion mobility spectrometer or separator 9, a second collision gas cell 10 and a Time of Flight mass analyser 11.

The ion source 5 may comprise an atmospheric pressure ion source, such as an Electrospray Ionisation ("ESI") ion source, or Matrix Assisted Laser Desorpotion Ionisation ("MALDI") ion source. The ion source 5 may be arranged and adapted to generate ions from a sample, which ions may then be passed into the vacuum pumping regions or chambers of the mass spectrometer 20.

The ion guide 6 may comprise an RF ion guide, which may comprise a plurality of electrodes, wherein an AC or RF voltage may be applied to the plurality of electrodes to confine ions radially within the ion guide 6. The ion guide 6 may be maintained at a sub-ambient pressure between about $10^{-3}$ mbar and about 2 mbar, for example using a vacuum pump connected to a chamber containing the ion guide 6. The ion guide 6 may be a travelling wave ion guide, wherein a plurality of transient DC voltages or voltage waveforms may be applied to the electrodes of the ion guide 6 to urge ions along the ion guide 6.

The mass filter 7 may comprise a quadrupole mass filter and may be arranged and adapted to filter ions according to their mass or mass to charge ratio. Ions may pass from the chamber containing the ion guide 6 to a chamber containing the mass filter 7 through an orifice between the two chambers. The chamber containing the mass filter may be maintained at a pressure of less than about $10^{-4}$ mbar.

Ions exiting the mass filter 6 may pass into a chamber containing the first collision gas cell 8 through an orifice between the chamber containing the mass filter 6 and the chamber containing the first collision gas cell 8. The chamber containing the first collision gas cell 8 (and/or the first collision gas cell 8) may be maintained at a pressure of about $5 \times 10^{-3}$ mbar. A collision gas may be supplied to the first collision gas cell 8, which collision gas may comprise argon.

Ions may enter the first collision gas cell 8 and collide with the gas contained within it, for example leading to fragmentation of the ions within the first collision gas cell 8 to produce daughter or fragment ions. The first collision gas cell 8 may be evacuated of its collision gas, and may operate as an ion guide such that, in some modes of operation ions do not undergo any type of fragmentation within the first collision gas cell 8. In such modes of operation the pressure within the first collision gas cell 8 may be between about $10^{-3}$ mbar and about 2 mbar.

Ions (e.g., parent or daughter ions) may pass from the collision gas cell 8 into the chamber containing the ion mobility spectrometer or separator 9, for example through an orifice between the chamber containing the first collision gas cell 8 and the chamber containing the ion mobility spectrometer or separator 9.

The ion mobility spectrometer or separator 9 may comprise a drift cell which may be maintained at about 2 mbar of a drift gas, for example comprising nitrogen. The ion mobility spectrometer or separator 9 may comprise a plurality of electrodes, wherein an AC or RF voltage may be applied to the plurality of electrodes to confine ions radially within the ion mobility spectrometer or separator 9. The ion mobility spectrometer or separator 9 may be maintained at a sub-ambient pressure between about $10^{-3}$ mbar and about 2 mbar, for example using a vacuum pump connected to a chamber containing the ion mobility spectrometer or separator 9. The ion mobility spectrometer or separator 9 may be a travelling wave ion guide, wherein a plurality of transient DC voltages or voltage waveforms may be applied to the electrodes of the ion mobility spectrometer or separator 9 to urge ions along the ion mobility spectrometer or separator 9.

Ions may be separated according to their ion mobility within the ion mobility spectrometer or separator 9, for example by being driven through the ion mobility spectrometer or separator 9 against the drift gas.

The separated ions may then be passed into the second collision gas cell 10 via an orifice between the chamber containing the ion mobility spectrometer or separator 9 and a chamber containing the second collision gas cell 10. The chamber containing the second collision gas cell 10 (and/or the second collision gas cell 10) may be maintained at a pressure of about $5 \times 10^{-3}$ mbar. A collision gas may be supplied to the second collision gas cell 10, which collision gas may comprise argon.

Ions may enter the second collision gas cell 10 and collide with the gas contained within it, for example leading to fragmentation of the ions within the second collision gas cell 10 to produce daughter or fragment ions. The second collision gas cell 10 may be evacuated of its collision gas, and may operate as an ion guide such that, in some modes of operation ions do not undergo any type of fragmentation within the second collision gas cell 10. In such modes of operation the pressure within the second collision gas cell 10 may be between about $10^{-3}$ mbar and about 2 mbar.

Ions that have been separated according to their ion mobility in the ion mobility spectrometer or separator 9 may be passed to the Time of Flight mass analyser 11 through an orifice between the chamber containing the ion mobility spectrometer or separator 9 and the Time of Flight mass analyser 11. The Time of Flight mass analyser 11 and/or may be maintained at less than about $10^{-6}$ mbar.

The Time of Flight mass analyser 11 may comprise an orthogonal acceleration Time of Flight mass analyser 11, in which ions may be sequentially fed to the Time of Flight mass analyser 11 in a direction of motion, and then accelerated (e.g., by a pusher electrode) along an axis perpendicular to the direction of motion and into a Time of Flight region.

In accordance with the disclosure, one or more substances may be included in the drift gas of the ion mobility spectrometer or separator 9.

The one or more substances (e.g., liquid methanol) may be introduced via a syringe pump 12 directly into the ion mobility spectrometer or separator 9 or the drift cell of the ion mobility spectrometer or separator 9. Additionally, one or more buffer gases may be introduced into the ion mobility spectrometer or separator 9 or the drift cell of the ion mobility spectrometer or separator 9. The buffer gas may be intermixed with the one or more substances prior to its introduction into the ion mobility spectrometer or separator 9 or the drift cell thereof. Alternatively, the buffer gas (e.g., nitrogen) may be introduced via a separate, buffer gas inlet 13.

The buffer gas may be introduced into the ion mobility spectrometer or separator 9 or the drift cell thereof simultaneously with the one or more substances.

In some experiments, the pressure of gas inside the ion mobility spectrometer or separator 9 has been measured with a capacitance manometer, and the various flow rates according to a particular experimental setup have been analysed.

Under normal operational conditions a flow of about 90 ml/min of nitrogen may be introduced into the ion mobility spectrometer or separator 9, which optionally results in a recorded pressure of about 2.93 mbar.

A temperature of about 298 K and pressure of about 1000 mbar is assumed for the following calculations.

About 90 ml of nitrogen contains approximately 0.004 moles of nitrogen gas. As nitrogen has a molecular weight of 28 this is equivalent to about 0.113 g of nitrogen gas per minute. Methanol has a molecular weight of 31 and a density of about 791.80 kg/m$^3$. Therefore, 0.004 moles of methanol is equivalent to about 0.125 g methanol liquid which has a volume of about 157 µL methanol.

Therefore, direct introduction of methanol into the ion mobility spectrometer or separator 9 at a rate of about 157 µL/min may result in the same number density (number of gas molecules) as 90 ml/min of nitrogen.

Figure 4:
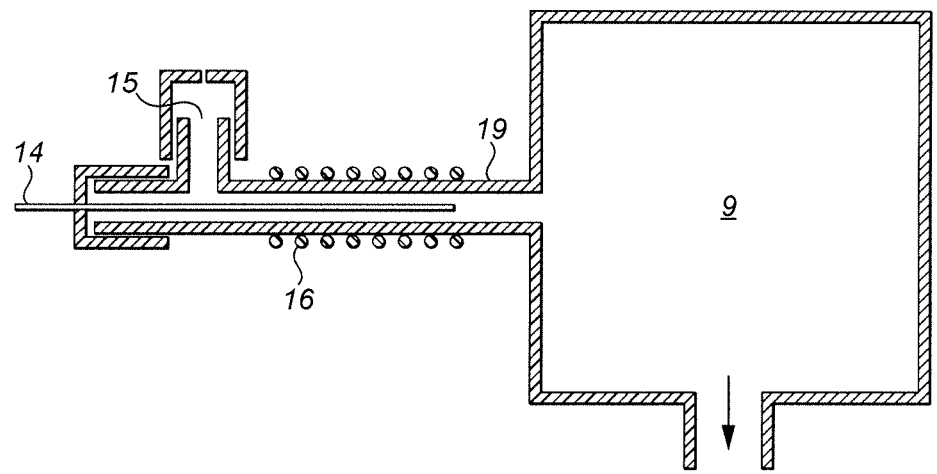
FIG. 4 shows a capillary device according to an embodiment.

FIG. 4 shows an embodiment of an apparatus in accordance with the disclosure.

The apparatus may be used for stable introduction of one or more substances, for example an additive such as methanol, into the drift cell or region of the ion mobility spectrometer or separator 9, wherein the one or more substances exist as a liquid at atmospheric pressure and room temperature, and wherein the one or more substances have a boiling or sublimation point less than said operating temperature of the ion mobility spectrometer or separator, at said reduced pressure.

A source of the one or more substances, e.g., a tank containing the one or more substances (e.g., in liquid phase) may be provided and this source may be in fluid communication with a capillary 14, for example a fused silica or metal capillary. The capillary 14 may be located within a delivery tube 19 which is in fluid communication with the ion mobility spectrometer or separator 9. The delivery tube 19 may be a rigid or flexible tube. The delivery tube 19 is depicted schematically in FIG. 4, and may include curves or bends, and/or may include an attachment portion for connecting to the ion mobility spectrometer or separator 9.

A pump may be provided and may be arranged and adapted to drive, push, propel or draw the one or more substances through the capillary 14 and into the delivery tube 19 (if provided). Alternatively, or additionally a high pressure end of the capillary 14 may be placed in the solution external to a vacuum portion of the ion mobility spectrometer or separator 9. This optionally allows the pressure differential between the vessel containing the liquid additive and the ion mobility spectrometer or separator 9 to draw the liquid additive through the capillary 14. The vessel containing the liquid additive may be pressurized above atmospheric pressure to alter the rate at which liquid is drawn or forced through capillary 14.

The one or more substances may be in liquid form, or held in a liquid solvent and the liquid or solvent may be continuously drawn through the capillary, optionally using a pump (not shown). The pump may be positioned at any suitable location in the apparatus shown in FIG. 4 such that it could be configured to drive, push, propel or draw liquid through the capillary. Alternatively, or additionally, the liquid or solvent may be drawn through the capillary using the pressure differential between the entrance to the capillary and the ion mobility spectrometer or separator. The flow may be controlled such that the pressure within the ion mobility spectrometer or separator remains substantially constant, for example over an extended period of time such as an experimental run.

If desired a separate buffer gas may be introduced via a buffer gas inlet 15. The buffer gas inlet 15 may be introduced in any manner such that the buffer gas mixes with the liquid emerging from the capillary before being passed into the mass spectrometer.

In FIG. 4 the buffer gas inlet 15 forms part of the delivery tube 19. The capillary 14 may be positioned within the delivery tube 19, and the inlet 15 may be positioned behind the exit of the capillary 14 into the delivery tube 19. This means that the flow of buffer gas can be well formed prior to the point at which it mixes with the liquid emerging from the capillary 14.

The delivery tube may be coaxial to the capillary 14 to optionally assist vaporisation of the liquid additive as it exits the capillary 14, and/or allow efficient sweeping out of the vapourised additive if the flow of liquid through capillary 14 is turned off. The capillary 14 may be held in place by one or more devices located at least partially within the delivery tube 19. The one or more devices may locate the capillary 14 centrally and/or along the longitudinal axis of (and/or coaxially to) the delivery tube 19, at least at the exit of the capillary 14 into the delivery tube 19, so that a uniform gap may exist between the capillary 14 and the interior walls of the delivery tube 19. This can assist in the nebulisation of liquid as it emerges from the capillary 14.

The present disclosure may allow polar liquid dopants to be introduced when required and equilibrium conditions without the presence of the liquid vapour to be rapidly established when the flow is interrupted.

In various embodiments a heater 16 may be used to optionally assist stable vaporisation conditions. Although the liquid exiting the capillary may naturally vapourise due to the reduction in pressure, and optionally remain in a gaseous state at room temperature, it has been found that uncontrolled vaporisation within the capillary 14 can cause unstable delivery of vapour. For example, delivery of volatile liquids such as acetone with flow rates greater than about 2 μL/min may result in unstable delivery of vapour in the absence of a heater 16. For example, the liquid emerging from the capillary 14 or being transferred along the delivery tube 19 may sputter. When using methanol, heating may be required for flow rates above about 40 μL/min. For water this value may be higher, although unstable flows may still occur absent of heating.

Mixing a proportion of more volatile liquid with less volatile liquid, for example about 10% acetone in water may allow more flexibility with respect to the stable introduction of very polar or reactive liquid additives, or very volatile liquid additives or soluble gasses such as carbonated water or carbon dioxide dissolved in water. Various embodiments may involve the introduction of a plurality of substances including water or methanol, and at least one other substance, wherein the addition of water or methanol may assist in the stable delivery of the at least one other substance. For example, the use of water or methanol may stabilise the delivery of the at least one other substance into the delivery tube 19 or ion mobility spectrometer or separator 9.

The heater 16 may allow the vaporisation of the liquid additive to be controlled within the capillary 14 to stabilize the vapour delivery. Various embodiments may include adjusting the temperature of the heater 16 to stabilise the delivery of the one or more substances into the delivery tube 19 or ion mobility spectrometer or separator 9, or until the delivery of the one or more substances into the delivery tube 19 or ion mobility spectrometer or separator 9 is stabilised.

The heater 16 may comprise a resistive heater and may be used in a similar way to Thermospray probes, where a heater is used for ionization. A counter electrode may be held at a potential difference of about 10 V to greater than about 1000 V with respect to the exit of the capillary, which counter electrode may be placed downstream of the capillary, for example to assist electrostatic nebulisation.

Other methods of controlling the delivery of the one or more substances can be envisaged, such the use of an ultrasonic device arranged and adapted to apply ultrasound to the liquid within the capillary 14. An ultrasound device, for example a transducer may be arranged and adapted to apply ultrasound energy to liquid emerging from the capillary 14. Various embodiments may include adjusting the ultrasound energy to stabilise the delivery of the one or more substances into the delivery tube 19 or ion mobility spectrometer or separator 9, or until the delivery of the one or more substances into the delivery tube 19 or ion mobility spectrometer or separator 9 is stabilised.

Figure 5:
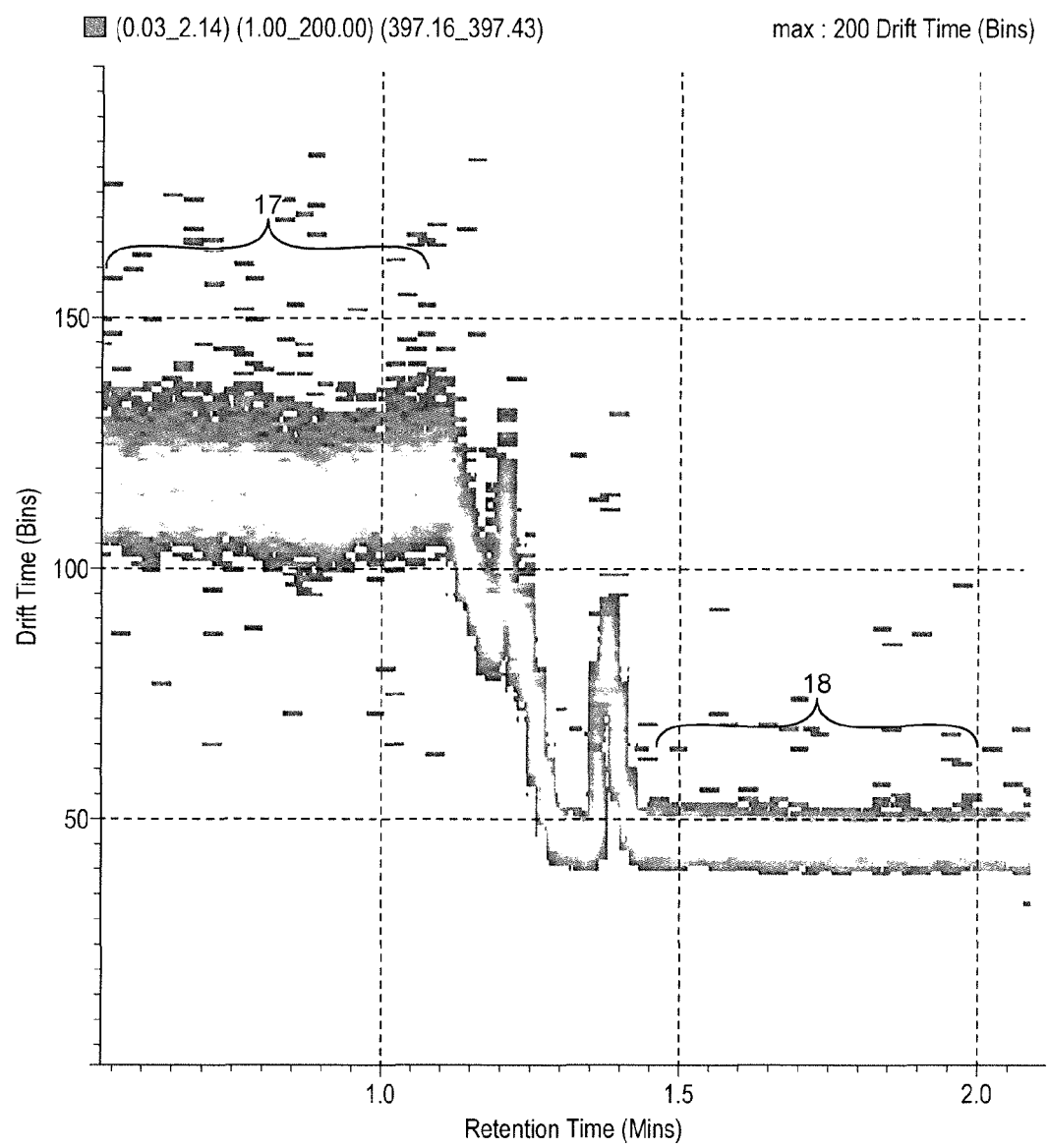
FIG. 5 shows a drift time versus retention/infusion time plot.

FIG. 5 shows a graph of retention time versus drift time for the direct infusion of methanol into an ion mobility spectrometer or separator in a setup similar to that shown in FIG. 4, while simultaneously or separately introducing nitrogen buffer gas. The methanol may be introduced into the ion mobility spectrometer or separator 9 at about 40 μl/min, while the nitrogen may be introduced at about 90 ml/min. The methanol may be introduced using a syringe pump and/or capillary 14.

In the data presented the composition of the drift gas was varied between pure nitrogen to a mixture of nitrogen and methanol. All other ion mobility parameters or conditions, such as a travelling wave velocity and amplitude, were optionally held constant. Pressure within the ion mobility spectrometer or separator 9 may be recorded using a capacitance manometer.

A solution of about 200 pg/μL of Leucine Enkephalin was infused at about 5 μL/min and then ionized using positive Electrospray ionization. The $[M+H]^+$ molecular ion at a mass to charge ratio ("m/z") of 556.3 was isolated using a quadrupole mass filter 7. The parent or precursor ion was fragmented in collision cell (similar to the first collision cell 8 shown and described in respect of FIG. 3) by Collision Induced Dissociation ("CID") prior to ion mobility separation of the product ions in an ion mobility spectrometer or separator. The mass spectra were recorded using an orthogonal acceleration Time of Flight mass analyser, similar to the orthogonal acceleration Time of Flight mass analyser shown and described in respect of FIG. 3.

FIG. 5 shows a drift time versus infusion time plot of the product ion at nominal m/z 397 from Leucine Enkephalin. In region 17 about 40 μl/min of methanol was directly infused into the ion mobility spectrometer or separator 9, while simultaneously introducing about 90 ml/min of nitrogen buffer gas. In region 18 the flow of methanol was turned OFF while maintaining the flow of about 90 ml/min of nitrogen.

It can be seen that there is a clear reduction in the drift time for this product ion when the methanol flow is stopped.

The pressure within the ion mobility spectrometer or separator 9 in region 17 may be about 3.45 mbar, and the pressure within the ion mobility spectrometer or separator 9 in region 18 may be about 2.93 mbar.

About 40 μl of methanol may represent about 0.001 moles of methanol which may be combined with about 0.004 moles of nitrogen gas. The total number of moles of nitrogen+methanol in this case should be about 0.005 moles. Therefore the pressure within the ion mobility spectrometer or separator 9 would be expected to change from about 2.93 mbar with no methanol to about 3.66 mbar with about 40 μl/min of methanol.

The pressure rise may be of the expected order. However, the discrepancy (about 3.45 mbar instead of about 3.66 mbar) may be due to differences in the pumping speed of the two different gasses or may be due to inaccuracies in the flow rates.

Figure 6A:
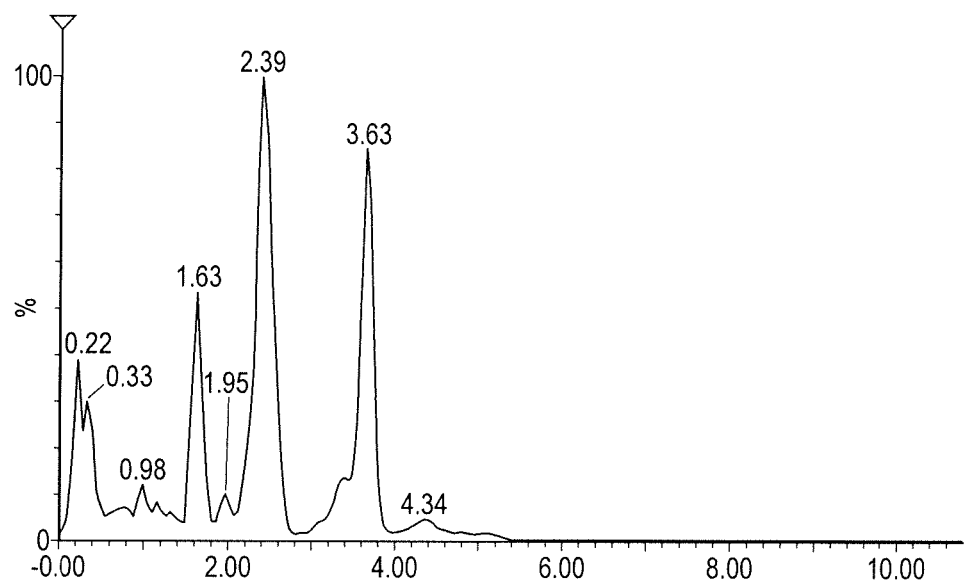
FIG. 6A shows a mobility spectrum for the product ions of Leucine Enkephalin without methanol introduction and FIG. 6B shows a mobility spectrum for the product ions of Leucine Enkephalin with methanol introduction.
Figure 6B:
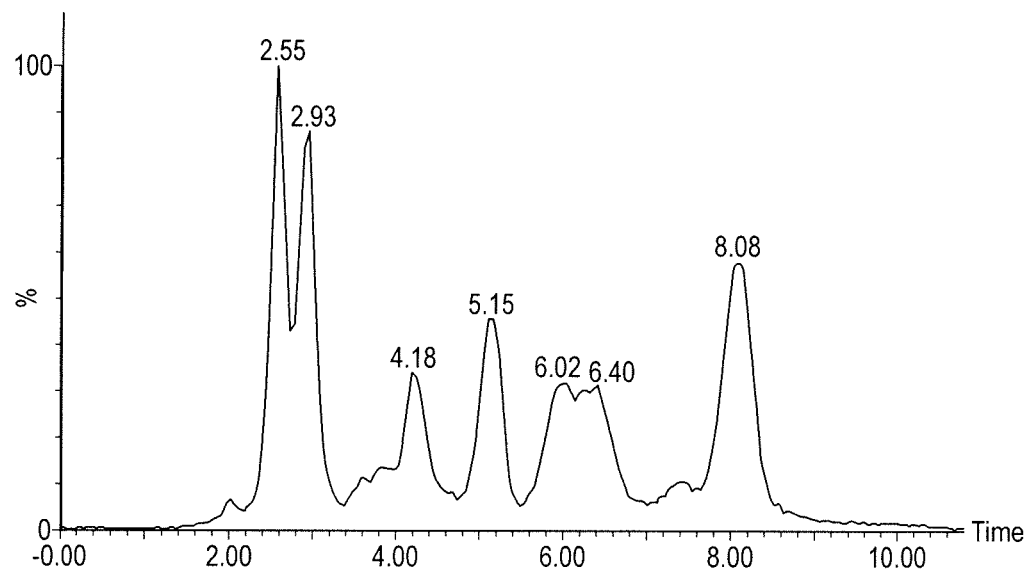

FIG. 6A shows a mobility spectrum for the product ions of Leucine Enkephalin without methanol introduction and FIG. 6B shows a mobility spectrum for the product ions of Leucine Enkephalin with methanol introduction.

Figure 7A:
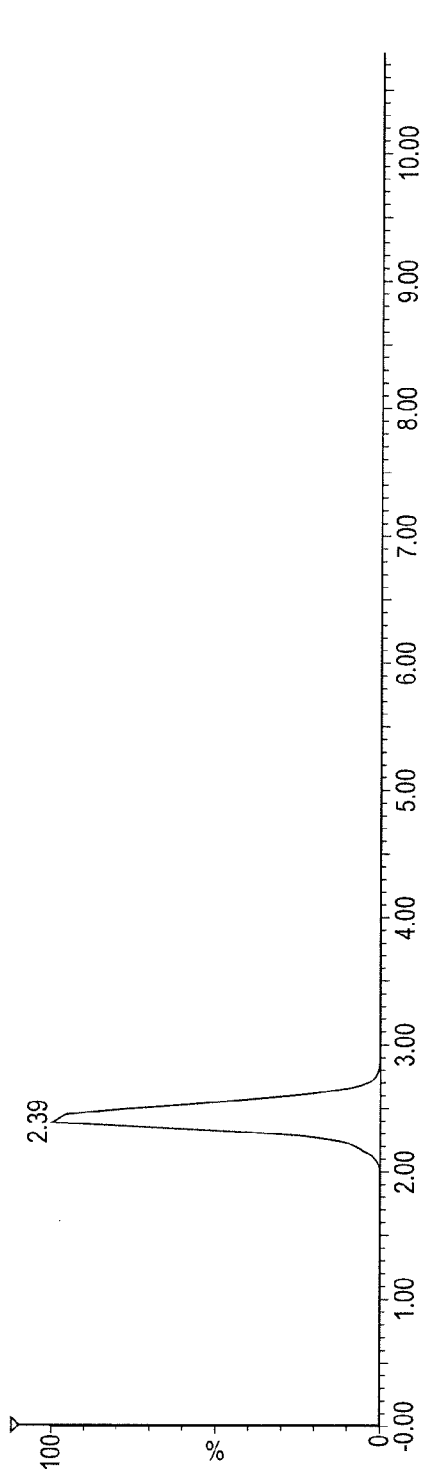
FIG. 7A shows a mobility spectrum for an "a4" product ion at nominal m/z 397 from Leucine Enkephalin without introduction of methanol and FIG. 7B shows a mobility spectrum for an "a4" product ion at nominal m/z 397 from Leucine Enkephalin with introduction of methanol.
Figure 7B:
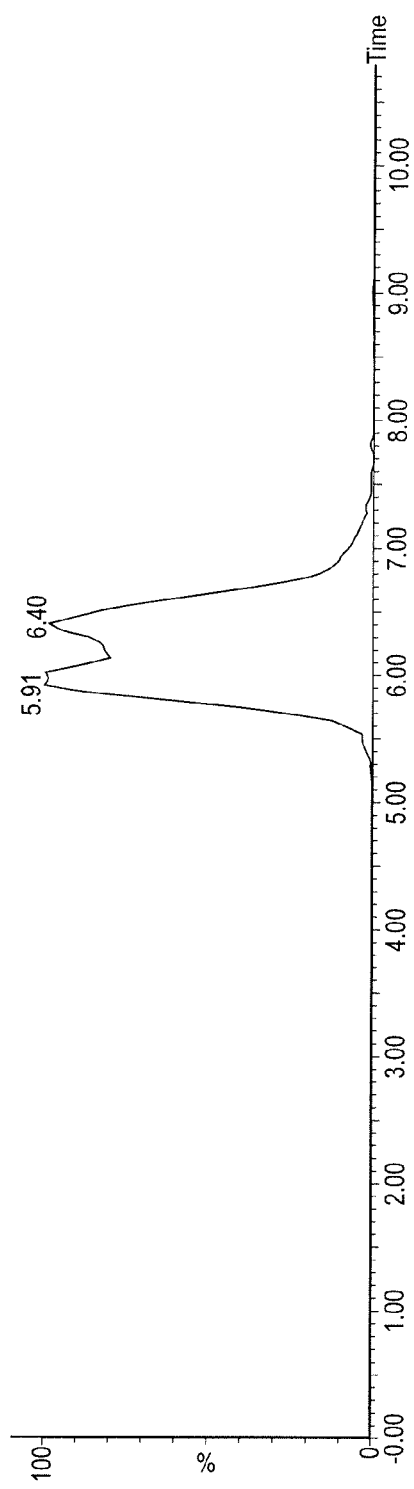

FIG. 7A shows a mobility spectrum for an "a4" product ion at nominal m/z 397 from Leucine Enkephalin without introduction of methanol and FIG. 7B shows a mobility spectrum for an "a4" product ion at nominal m/z 397 from Leucine Enkephalin with introduction of methanol.

When methanol is introduced, a doublet can be seen for the "a4" product ion. It has been suggested that this ion species, at m/z 397, can exist in both cyclic and linear forms. The doublet shown in FIG. 7B may indicate the present of two different ion species which interact differently with the methanol vapour. The presence of a high drift time tail in FIG. 7B may suggest the possibility of the presence additional structures in lower abundance at this m/z value.

Reference is made to J. Phys. Chem. A, 2008, 112 (6), pp. 1286-1293, DOI: 10.1021/jp0763937.

Figure 8:
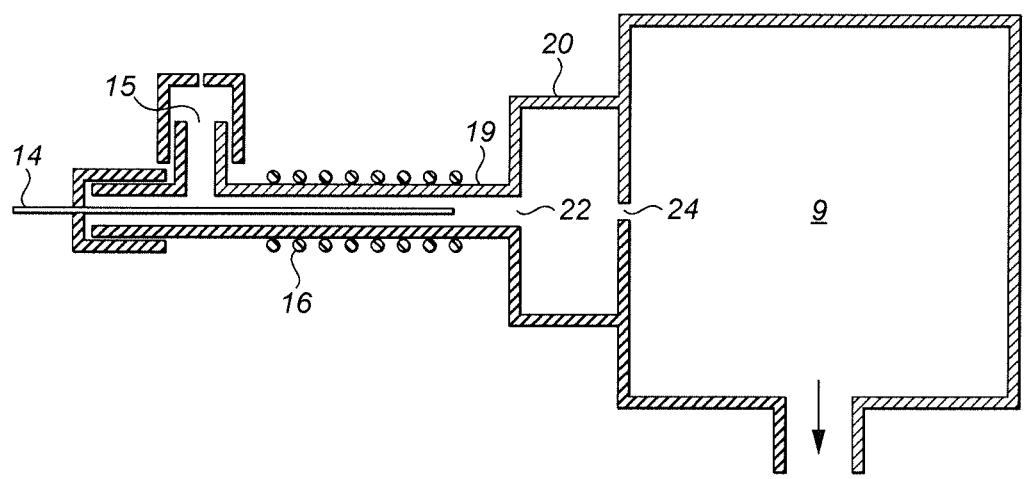
FIG. 8 shows a capillary device according to an embodiment.

FIG. 8 shows an embodiment of an apparatus in accordance with the present disclosure. The embodiment of FIG. 8 includes all of the features of the FIG. 4 embodiment, as well as the additional feature of a chamber 20 (or reservoir, or increased volume chamber or portion). The chamber 20 may be for stabilising the flow of buffer gas and the one or more substances (i.e., the drift gas) prior to its introduction into the ion mobility spectrometer or separator 9.

The chamber 20 may be located downstream of the end of the capillary 14 and/or delivery tube 19. The chamber 20 may comprise an inlet 22 in fluid communication with the capillary 14 and/or delivery tube 19, and an outlet 24 in fluid communication with the ion mobility spectrometer or separator 9. The outlet 24 may be arranged and adapted to release drift gas directly into the ion mobility spectrometer or separator 9. The chamber 20 may be located immediately after the delivery tube 19, or the chamber 20 may form the downstream end of the delivery tube 19.

The chamber 20 may have an increased diameter or cross-sectional area compared to the capillary 14 and/or delivery tube 19. The outlet 24 of the chamber 20 may have a width (e.g., through a centre point of the outlet 24), diameter or cross-sectional area (for example a smallest width, diameter or cross-sectional area) that is less than that of the capillary 14 and/or delivery tube 19.

The outlet 24 may have a width, diameter or cross-sectional area (for example a smallest width, diameter or cross-sectional area) that is less than 5%, 10%, 15% or 20% of the largest width, diameter or cross-sectional area of the chamber 20. The width, diameter or cross-sectional area (for example a smallest width, diameter or cross-sectional area) of the outlet 24 may be less than 10%, 20%, 30%, 40%, 50%, 60%, 70%, 80% or 90% of the width, diameter or cross-sectional area (for example the smallest width, diameter or cross-sectional area) of the inlet 22.

In use a fluid may be travelling through the delivery tube 19, which fluid may be a drift gas and may include the one or more substances and/or a buffer gas. The fluid may enter the chamber 20 through the inlet 22, and may expand, for example due to the increased volume (or width, diameter or cross-sectional area) of the chamber 20. The constituents of the fluid, for example the one or more substances and/or a buffer gas may intermix within the chamber 20. The fluid (e.g., once intermixed) may then pass through the outlet 24 of the chamber 20 and into (e.g., directly into) the ion mobility spectrometer or separator 9.

It will be appreciated that the chamber 20 can help to stabilise the mixture of buffer gas and one or more substances prior to its introduction into the ion mobility spectrometer or separator 9. Should the mixture sputter upon exiting the delivery tube 19 in the FIG. 4 embodiment, for example, this can lead to instabilities inside the ion mobility spectrometer or separator 9. Providing a chamber 20 as shown in FIG. 8 can help to eliminate this sputter, since the mixture will sputter into the chamber 20 rather than the ion mobility spectrometer or separator 9. Once the mixture has stabilised, it can then be transferred into the ion mobility spectrometer or separator 9 through the outlet 24.

In some instances the outlet 24 can be provided such that its dimensions are small relative to the inlet 22 (as described above). This can ensure that the buffer gas and one or more substances are mixed within the chamber as the gas expands upon exiting the delivery tube 19 into the inlet 22 of the chamber 20, and its flow out of the chamber 20 may be restricted by the smaller outlet 24.

The additional chamber 20 acts as an expansion reservoir prior to gas flow into the ion mobility spectrometer or separator 9 through the outlet 24 (which may be termed conductance orifice). The pressure within chamber 20 may be, in use, slightly higher than the pressure in the ion mobility spectrometer or separator 9 (or chamber containing the ion mobility spectrometer or separator 9).

The chamber 20 may act to damp or smooth out any short tem instabilities or variations in flow during introduction of the one or more substances via the capilliary 14, which can allow improved stability of the pressure within the ion mobility spectrometer or separator 9.

Gradients in vapour composition or time dependent changes of vapour composition may be applied using flow control equipment in the liquid additive delivery equipment, such as in capillary 14. One or more flow control devices (e.g., a pump or variable flow restrictor) may be located within the delivery tube 19 and/or capillary, and the one or more flow control devices may be arranged and adapted to adjust the flow rate of the liquid through the capillary 14 and/or the gas flow through the delivery tube 19.

It will also be appreciated that substances that are solids at room temperature and pressure, but vapour within the ion mobility spectrometer or separator at its reduced pressure (e.g. below about 10 mbar) can be introduced, for example continuously introduced into the ion mobility spectrometer or separator 9, for example to act as reactants or dopants. In these embodiments the solid substance may be dissolved into a suitable solvent and introduced with the liquid flow as described.

As long as the additive substance (liquid or solid) remains in vapour form at reduced pressure then condensation within the ion mobility spectrometer or separator 9 will be eliminated or minimised. This allows a very wide range of compounds to be continuously introduced into the ion mobility spectrometer or separator 9, for example an RF confined region thereof, to act as reactants or ion mobility dopants.

In addition, compounds which are solids at room temperature and pressure but which sublime at temperatures lower than the operating temperature of the ion mobility spectrometer or separator, at its reduced pressure (e.g. below about 10 mbar) may be continuously introduced, for example dissolved within a suitable solvent.

The method and apparatus disclosed herein may relate to the addition of polar dopants into a reduced pressure ion mobility spectrometer or separator 9, for example an RF confined ion mobility spectrometer or separator. The method and apparatus disclosed herein may additionally or alternatively be used to introduce liquid or dissolved solid sample into an ion guide or ion trapping region of a mass spectrometer, for example an RF confined ion guide or ion trap.

The method and apparatus disclosed herein may additionally or alternatively be used to perform ion-molecule reactions of many different types. For example hydrogen deuterium exchange may be performed within an ion guide or ion trapping region of a mass spectrometer, for example an RF confined ion guide or ion trap, using deuterated water rather than using e.g. a gaseous sample such as deuterated ammonia. Other gas phase ion-molecule reactions may be envisaged.

In this manner, various embodiments may relate to a method of guiding or trapping ions, comprising operating an ion guide or ion trap at a reduced pressure and at an operating temperature less than about 40° C., and providing a gas within the ion guide or ion trap, wherein the gas comprises one or more substances that exist as a liquid at atmospheric pressure (optionally about 1013 mbar) and room temperature (optionally about 20° C.) and wherein said one or more substances have a boiling or sublimation point less than said operating temperature of said ion mobility spectrometer or separator, at said reduced pressure.

Although the present invention has been described with reference to preferred embodiments, it will be understood by those skilled in the art that various changes in form and detail may be made without departing from the scope of the invention as set forth in the accompanying claims.

The invention claimed is:

1. A method of separating ions comprising:
   operating an ion mobility spectrometer or separator at a reduced pressure and at an operating temperature less than 40° C.; and
   providing a drift gas within said ion mobility spectrometer or separator, wherein said drift gas comprises one or more substances that exist as a liquid at atmospheric pressure and room temperature and wherein said one or more substances have a boiling or sublimation point less than said operating temperature of said ion mobility spectrometer or separator, at said reduced pressure.

2. A method as claimed in claim 1, further comprising operating said ion mobility spectrometer or separator at a pressure less than 10 mbar.

3. A method as claimed in claim 1, wherein between 1-100% of said drift gas consists of said one or more substances.

4. A method as claimed in claim 1, wherein less than 1% of said drift gas consists of said one or more substances.

5. A method as claimed in claim 1, wherein said drift gas further comprises a buffer gas and wherein said one or more substances comprise or consist of an additive or dopant to said buffer gas for ion mobility spectrometry ("IMS") selectivity.

6. A method as claimed in claim 5, further comprising mixing said one or more substances with said buffer gas prior to introducing said buffer gas into said ion mobility spectrometer or separator.

7. A method as claimed in claim 5, further comprising introducing said one or more substances into said ion mobility spectrometer or separator separately to said buffer gas.

8. A method as claimed in claim 1, further comprising introducing said one or more substances into said ion mobility spectrometer or separator via a capillary, wherein an entrance of said capillary is at atmospheric pressure and room temperature.

9. A method as claimed in claim 8, further comprising heating said capillary as said one or more substances are drawn through said capillary to assist vaporisation of said one or more substances prior to entering said ion mobility spectrometer or separator.

10. A method as claimed in claim 8, wherein said capillary is made from metal or a thermally-conductive material.

11. A method as claimed in claim 9, wherein said step of heating said capillary comprises resistively heating said capillary.

12. A method as claimed in claim 8, further comprising driving, pushing, propelling or drawing the one or more substances through the capillary using a pump, or the pressure differential between a source of the one or more substances and the ion mobility spectrometer or separator.

13. A method as claimed in claim 8, wherein said one or more substances vapourise upon exiting said capillary due primarily to the reduction in pressure between said capillary and said ion mobility spectrometer or separator.

14. A method as claimed in claim 8, further comprising positioning said capillary within a delivery tube, wherein said delivery tube exits into said ion mobility spectrometer or separator.

15. A method as claimed in claim 14, wherein said capillary is positioned coaxially within said delivery tube.

16. A method as claimed in claim 14, further comprising introducing a or said buffer gas into said delivery tube.

17. A method as claimed in claim 14, wherein said buffer gas is introduced into said delivery tube via a buffer gas inlet in said delivery tube, and said buffer gas inlet is positioned behind an exit of said capillary into said delivery tube.

18. A method as claimed in claim 1, wherein said one or more substances are held in a gaseous state within said ion mobility spectrometer or separator due to said reduced pressure.

19. A method as claimed in claim 1, wherein said ion mobility spectrometer or separator is not heated or is unheated.

20. A method as claimed in claim 1, wherein said one or more substances would transition to a liquid or solid state within said ion mobility spectrometer or separator if said ion mobility spectrometer or separator were at atmospheric pressure.

21. A method as claimed in claim 1, wherein said ion mobility spectrometer or separator comprises a plurality of electrodes, and wherein said method further comprises applying an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the electrodes forming said ion mobility spectrometer or separator in order to confine ions radially within said ion mobility spectrometer or separator.

22. A method of mass spectrometry or ion mobility spectrometry, comprising a method as claimed in claim 1.

23. A device for separating ions comprising:
   an ion mobility spectrometer or separator; and
   a control system arranged and adapted:
   (i) to operate said ion mobility spectrometer or separator at a reduced pressure and at an operating a temperature below 40° C.; and
   (ii) to provide a drift gas within said ion mobility spectrometer or separator, wherein said drift gas comprises one or more substances that exist as a liquid at atmospheric pressure and room temperature and wherein said one or more substances have a boiling or sublimation point less than said operating temperature of said ion mobility spectrometer or separator, at said reduced pressure.

24. A mass spectrometer comprising a device for separating ions as claimed in claim 23.

25. A method of guiding or trapping ions, comprising:
   operating an ion guide or ion trap at a reduced pressure and at an operating temperature less than about 40° C.; and
   providing a gas within the ion guide or ion trap, wherein the gas comprises one or more substances that exist as a liquid at atmospheric pressure and room temperature and wherein said one or more substances have a boiling or sublimation point less than said operating temperature of said ion guide or ion trap, at said reduced pressure.

26. A method as claimed in claim 25, wherein the one or more substances comprise a sample to be ionised, or comprise ionised sample to be analysed in a mass spectrometer.

27. A method as claimed in claim 25, wherein the ion guide or ion trap operates as an ion-molecule reaction device.

28. A method as claimed in claim 27, further comprising reacting ions within said ion-molecule reaction device to form adduct or product ions.

29. A method as claimed in claim 28, wherein said step of reacting ions comprises performing hydrogen-deuterium exchange within said ion-molecule reaction device.

30. A device for guiding or trapping ions, comprising:
an ion guide or ion trap; and
a control system arranged and adapted:
(i) to operate the ion guide or ion trap at a reduced pressure and at an operating temperature below 40° C.; and
(ii) to provide a gas within the ion guide or ion trap, wherein the gas comprises one or more substances that exist as a liquid at atmospheric pressure and room temperature and wherein said one or more substances have a boiling or sublimation point less than said operating temperature of said ion guide or ion trap, at said reduced pressure.

* * * * *